United States Patent [19]

Wallshein

[11] 4,186,487
[45] Feb. 5, 1980

[54] ORTHODONTIC ARCH WIRE

[76] Inventor: Melvin Wallshein, 8645 Bay Pkway., Brooklyn, N.Y. 11214

[21] Appl. No.: 792,866

[22] Filed: May 2, 1977

[51] Int. Cl.² ............................................. A61C 7/00
[52] U.S. Cl. ...................................................... 433/20
[58] Field of Search ...................................... 32/14 A

[56] References Cited
U.S. PATENT DOCUMENTS 3,838,515  10/1974  Paugh et al. .................... 32/14 A

OTHER PUBLICATIONS

"HI-T" Ad, "American Journal of Orthodontics", vol. 49, #12, Dec. 1963.

Primary Examiner—Russell R. Kinsey
Assistant Examiner—John J. Wilson
Attorney, Agent, or Firm—Frishauf, Holtz, Goodman & Woodward

[57] ABSTRACT

Orthodontic arch wires comprise at least one strand having a generally rectangular cross-section and which is loosely helically wound so that adjacent turns are separated from each other. The wide dimension of the strand travels helically along the length of the wire. In order to provide stiffer wires, two or more rectangular strands may be placed adjacent each other and helically wound, and/or, one or more round or other cross-sectional configuration strands may be wound with the rectangular wire, for example in the interstices thereof. The arch wire is arranged such that the outer dimension is substantially the same for all configurations. In a further embodiment, the rectangular strand is wound so as to have overlapping turns, the frictional forces developed at the overlapping portions of the turns increasing the stiffness of the arch wire. The arch wire may be flattened, for example by passing through orthogonally arranged pairs of rollers to provide an arch wire with a generally rectangular outer configuration so as to be useful in torquing applications.

41 Claims, 19 Drawing Figures

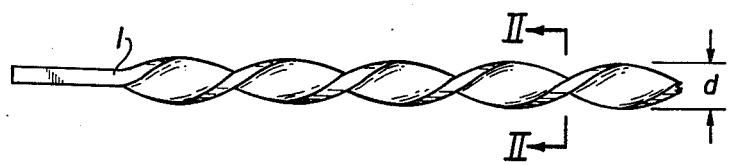 
FIG.1  FIG.2
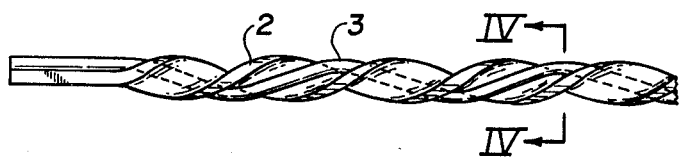 
FIG.3  FIG.4
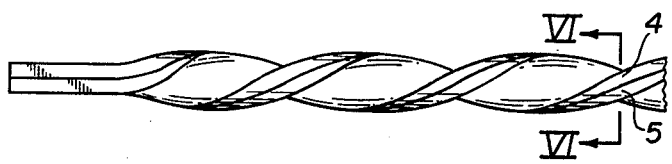 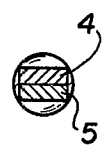
FIG.5  FIG.6
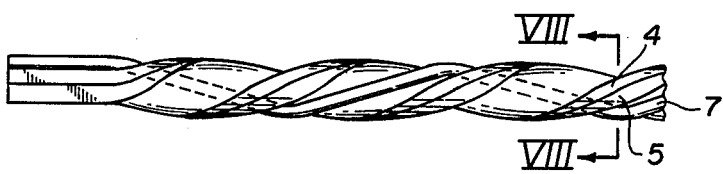 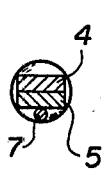
FIG.7  FIG.8
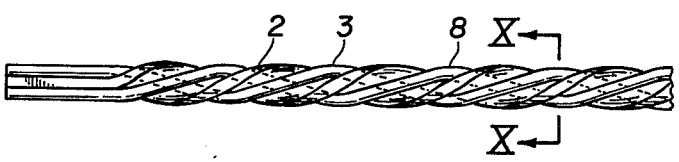 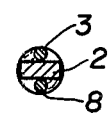
FIG.9  FIG.10
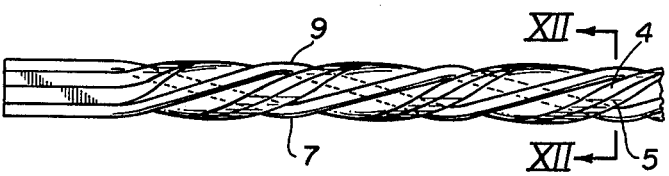 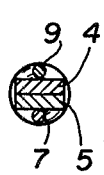
FIG.11  FIG.12

ORTHODONTIC ARCH WIRE

The present invention generally relates to orthodontic arch wires, and more particularly to an arch wire fabricated of one or more strands twisted to form a generally spiral configuration.

The following definitions apply to the specification and claims. "Stiffness" is the resistance of a material to bending or deformation. "Flexibility" is the ability of a material to bend or deform. "Plastic deformation" is a permanent change in the shape of a material. Once plastic deformation takes place, the removal of forces which caused the change in shape does not result in a return of the material to its original shape. The "elastic limit" of a material is the maximum load or deformation which can be applied to a material before plastic or permanent deformation takes place. "Resiliency" is the tendency of a flexed material to spring back to its original configuration on the removal of the flexing forces. "Working Range" is the range of deformation of a material where it retains its resiliency, up to a maximum deformation which can be sustained by a material without exceeding the elastic limit and becoming permanently deformed with loss of resiliency.

Orthodontic procedures usually require the placement of a bracket upon respective maloccluded teeth, either directly or via bands, and the employment of an arch wire for interconnecting the brackets relative to one another so that a force is transmitted from one bracket to the next and thereby to the teeth upon which the brackets are mounted. Today, the orthodontist is offered a wide variety of arch wires. The known arch wires vary both in size and material. An ideal arch wire must be flexible, but must have sufficient stiffness or "body" over long lengths so that it can serve as a relatively fixed anchoring or reference point to which other orthodontic devices can be connected. The flexibility, of course, is required so that the arch wire can be bent into the shape of an arch in the mouth. It is also desirable that the arch wire have a resiliency and sufficient range over short and long lengths in order to permit the application of local biasing forces to the teeth. Most wires do have the quality of resiliency over limited ranges of bending or deformation, i.e. over a limited working range, as defined above.

In orthodontic procedures wherein it is desired to precisely align a plurality of teeth, it is indispensable that the arch wire completely fill the opening of the bracket, which opening is generally rectangular in cross-section and has cross-section dimensions of approximately .0.22×0.028, 0.018×0.025 or 0.022×0.022 inches. Further, in some orthodontic procedures of the type mentioned above it is desired to use orthodontic wires of different flexibility or resiliency. If solid orthodontic wires are used, it is not possible to widely vary the range of resiliency and still completely fill the bracket opening to insure precise alignment of the teeth. In solid arch wires, the resiliency is generally a function of the cross-sectional dimension of the wire. If stranded wires are used, a similar problem exists in that it is not possible to provide a widely varying resiliency characteristic while also completely filling the bracket opening for all resiliencies of arch wires.

It is the object of the present invention to provide an arch wire configuration which is simple to manufacture and which is capable of providing different resiliencies with the same overall dimensions so as to always completely fill the opening of an orthodontic bracket.

It is a further object of the present invention to provide such an orthodontic arch wire in single strand as well as multiple strand form.

SUMMARY OF THE INVENTION

In accordance with a first aspect of the present invention an orthodontic arch wire comprises at least one strand having first and second cross-sectional dimensions, one cross-sectional dimension being greater than the other, the at least one strand being loosely helically wound so that adjacent turns are separated from each other or are in contact and such that the greater cross-sectional dimension of the strand helically winds along the wire. The helically wound wire has a maximum common outer dimension no greater than approximately 0.045 inches and the wire is made from a material sufficiently elastic to permit bending of the arch wire along the length thereof and to provide a predetermined stiffness over a long length. In a preferred embodiment, the at least one strand is helically wound without a lumen and is preferably rectangular in cross-section. A plurality of rectangular strands may be placed adjacent to each other and helically wound as described above and/or additional strands of, for example round cross-sectional wire, may be wound with the rectangular strands, for example in the interstices formed by the helically wound rectangular strands.

According to a further embodiment of the invention a preferably flat rectangular cross-sectional wire strand is helically wound such that adjacent turns overlap. A lumen may exist within the overlapping adjacent turns depending upon how tight the wire is wound. The overlapped portions, due to frictional forces, provide greater stiffness.

Any of the above discussed arch wires may be formed to present a generally rectangular outer configuration by, for example, passing them through two pairs of orthogonally arranged rollers to deform the outer shapes thereof to be generally rectangular. This enables the arch wire to be used to provide torquing forces.

BRIEF DESCRIPTION OF THE DRAWINGS

FIG. 1 illustrates a first embodiment of the present invention comprising a single rectangular strand wound in a spiral form;

FIG. 2 illustrates a cross-sectional view of the embodiment of FIG. 1 taken along the lines II—II in FIG. 1;

FIG. 3 illustrates another embodiment of the present invention comprising a single rectangular strand and a round strand wound together in spiral form;

FIG. 4 illustrates a cross-sectional view of the embodiment of FIG. 3 taken along the line IV—IV in FIG. 3;

FIG. 5 illustrates a further embodiment of the present invention comprised of two rectangular strands adjacent each other and wound in the form of a spiral;

FIG. 6 illustrates a cross-sectional view of the embodiment of FIG. 5 taken along the line VI—VI in FIG. 5;

FIG. 7 illustrates a further embodiment of the present invention comprised of two rectangular strands and a round strand, all wound together in spiral form;

FIG. 8 illustrates a cross-sectional view of the embodiment of FIG. 7 along the line VIII—VIII in FIG. 7;

FIG. 9 illustrates another embodiment of the present invention comprised of one rectangular strand and two round strands, all wound together in a spiral form;

FIG. 10 illustrates a cross-sectional view of the embodiment of FIG. 9 along the line X—X in FIG. 9;

FIG. 11 illustrates yet another embodiment of the present invention comprised of two rectangular strands and two round strands, all wound together in spiral form;

FIG. 12 illustrates a cross-sectional view of the embodiment of FIG. 11 along the line XII—XII in FIG. 11;

DETAILED DESCRIPTION

Figure 16:
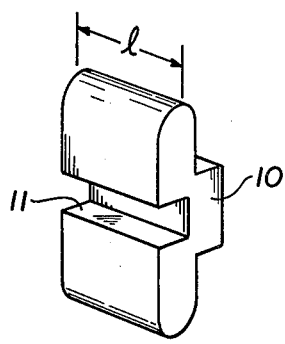
FIG. 16 illustrates an example of a typical bracket with which the arch wire of the present invention is usable.

Referring to FIGS. 1 and 2, a single rectangular strand of wire 1 is wound in a spiral form so that in cross-section, the wound wire exhibits a maximum external diameter "d" which corresponds substantially exactly with the internal dimension of an opening of an orthodontic bracket so that the spiral wound strand fits securely in the opening of a bracket without excessive clearance or play. Adjacent turns of the wire 1 are separated from each other, the separation between adjacent turns defining a helically winding void space along the longitudinal axis of the wire. FIG. 16 shows a typical bracket with which orthodontic wires of the present invention are usable. Other brackets could obviously be used. The bracket 10 of FIG. 16 has an arch wire receiving opening 11 formed therein, the length of the opening being designated by "l". The orthodontic wire of FIG. 1 is wound with the spiral arranged preferably such that at least 2-3 turns of the spiral fit within the length l of the opening 11 of the bracket 10. This insures a precise fit within the bracket opening without excessive wobbling or play of the wire therein. Such prevention of excessive wobbling enables precise alignment of teeth to be obtained when using the orthodontic arch wire of the present invention. Less than 2-3 turns could also be arranged in the length "l". In such a case it may become necessary to adjust the longitudinal relationship of the wire relative to the bracket 10 so that a desired fit in the bracket opening 11 is achieved. A typical value of l is approximately 0.050 inches, although it may be larger or smaller.

If it is desired to utilize a wire of different resiliency, then it is merely necessary to choose a wire with a thinner rectangular cross-section, the wire having at least one dimension of sufficient length such that the outer diameter of the wire, when wound in a spiral, has the dimension d as shown in FIG. 1. Thus, varying degrees of resiliency or flexibility can be obtained while still retaining the overall effective outer diameter of the wire at the proper size for secure non-wobbling fit within an opening 11 of an orthodontic bracket 10.

The wire strand 1 illustrated in FIGS. 1 and 2 typically has a cross-section of about $0.011 \times 0.022$ inches, as seen more clearly in FIG. 2. To provide a twisted wire with greater resiliency, the smaller 0.011 dimension can be reduced. Alternatively, the smaller 0.011 dimension can be increased to increase the stiffness of the wire. Other dimensions and various ratios may be used to provide wires having different degrees of resiliency and other orthodontic characteristics. Also, the size of the wire strand used will depend upon the particular type of wire and its inherent structural characteristics.

FIGS. 3 and 4 illustrate another embodiment of the invention comprising a flat rectangular wire strand 2, which is similar to strand 1 of FIGS. 1 and 2, and a round strand 3. The flat strand 2 is wound in a spiral similar to that of FIG. 1 and the strand 3 is also wound in a spiral interleaved with the strand 2. In the FIG. 3 embodiment, the spacing between adjacent turns also defines a helically winding void space along the longitudinal axis of the wire. The arrangement of FIGS. 3 and 4 provides a stiffer composite structure than the single strand wire of FIG. 1, while still retaining the same overall outer dimensions. In some instances it is desirable to increase the stiffness of the wire by adding the round strand 3 as shown in FIGS. 3 and 4, rather than by increasing the thickness of the rectangular wire shown in FIG. 1.

In the embodiment of FIG. 3, the rectangular wire strand 2 has cross-sectional dimensions of $0.011 \times 0.022$ inches and the round wire 3 has a diameter of 0.009 inches. Other dimensions could be used, as desired, to provide wires of varying structural characteristics.

FIGS. 5 and 6 illustrate a further embodiment of the invention comprising two rectangular strands 4 and 5 which are side-by-side and wound in a spiral. This arrangement provides more stiffness than the wire of FIG. 1 and in some instances is desirable. The embodiment of FIGS. 5 and 6 is shown on a larger scale than those of FIGS. 1–4 for ease of illustration. The spiral of FIG. 5 is wound so that preferably at least 2–3 turns of the spiral fits within the length l of the opening 11 of the bracket 10 shown in FIG. 16 to prevent wobbling of the wire therein. The two wires of FIGS. 5 and 6 may, for example, have nominal dimensions of $0.011 \times 0.022$ inches; $0.0011 \times 0.018$ inches, or any other desired dimensions to provide composite wires suitable for special purposes.

FIGS. 7 and 8 illustrate an embodiment similar to that of FIGS. 5 and 6, but further providing a round strand 7 spirally wound in the interstices of the spiral formed by the rectangular wires 4,5. The arrangement of FIGS. 7 and 8 provides more stiffness than that of FIGS. 5 and 6.

FIGS. 9 and 10 illustrate another embodiment similar to that of FIGS. 3 and 4, but which further provides a second round strand 8 which is spirally wound with the rectangular strand 2 and the first round strand 3. As clearly seen in FIG. 10, the two round strands 3 and 8 are wound on opposite flat sides of the rectangular strand 2. This provides for a symmetrical and relatively smooth structure. Both round strands could alternately be provided on the same flat side of the rectangular strand 2. The arrangement of FIGS. 9 and 10 is still more resilient than that of FIGS. 3 and 4 and is desirable in some instances.

FIGS. 11 and 12 illustrate an embodiment similar to that of FIGS. 7 and 8, but comprising a second round strand 9. The round strand 9 adds additional stiffness to the wound wire of FIGS. 7 and 8 and in some instances is desirable.

As should be clear, while the flattened wires are shown as being rectangular in cross-section, it should be clear that they may take other forms, for example, oval or the like. A critical feature is that the flattened strands, shown as rectangular, should have different resiliencies in different directions so that when spirally wound a wire having the desired resiliency is obtained. While the round strands have been shown as having round cross-sections, it should be clear that other cross-sectional configurations could be used, such as oval, rectangular, or even irregular shapes.

Figures 13, 14:
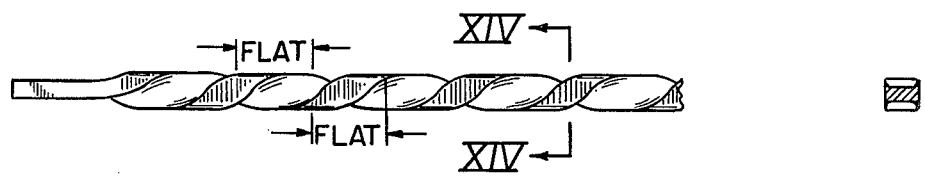
FIG. 13 illustrates an embodiment of the present invention formed so as to present a generally rectangular overall cross-section.
FIG. 14 illustrates a cross-sectional view of the embodiment of FIG. 13 along the line XIV—XIV in FIG. 13.
Figure 15:
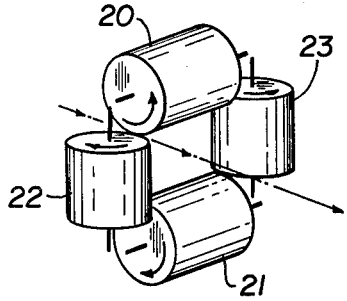
FIG. 15 illustrates one method of forming the overall generally rectangular shape of the embodiment of FIGS. 13 and 14.

FIGS. 13 and 14 illustrate the embodiment of FIGS. 1 and 2 after the helically wound strand has been passed through, for example, flattening rollers to form the the wound strand with a more generally rectangular outer cross-section. The flattened strand of FIGS. 13 and 14 may be achieved by passing the same through pairs of rollers arranged at right angles to each other, for example as shown in FIG. 15. The rollers press the sides of the helically wound strand so as to present a generally rectangular cross-section as illustrated in FIGS. 13 and 14.

The rollers 21-23 of FIG. 15 may be idler rollers with the strand forceably pulled therethrough, or the rollers may be driven so as to enhance movement of the strand therethrough.

Figure 17:
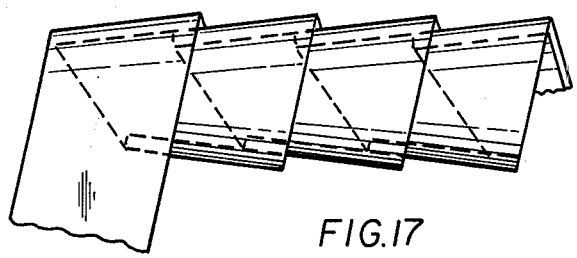
FIG. 17 illustrates a further embodiment of the present invention comprised of a single rectangular strand wound so that adjacent turns overlap.

FIG. 17 illustrates a further embodiment of the invention which comprises a rectangular cross-sectional strand, for example 0.002×0.020 inches, wound so that adjacent turns overlap each other so as to provide a hollow spiral-wound cylindrical orthodontic wire. The wire of FIG. 17, due to the overlapping nature of the turns, provides a wire with a high degree of stiffness. The greater the overlap between successive turns, the greater the stiffness of the resulting wound wire. This is due to the frictional forces developed at the overlapping turn portions when attempting to bend the wound wire. Other wire strand dimensions may be used and different degrees of overlap may be provided, as desired.

Figure 18:
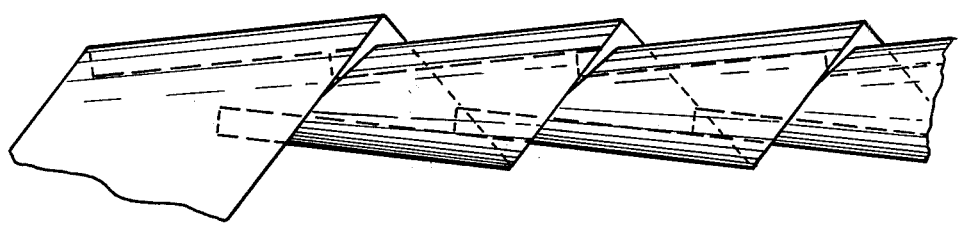
FIG. 18 illustrates a further embodiment of the present invention similar to that of FIG. 17 but utilizing a rectangular strand having different cross-sectional dimensions than the strand of FIG. 17.

FIG. 18 illustrates an embodiment of the invention similar to that of FIG. 17 except that the cross-sectional dimension of the wire strand is approximately 0.002×0.40 inches. The wire of FIG. 18 is more resilient (i.e., less springy) than the wire of FIG. 17.

The dimensions given above for the wires of FIGS. 17 and 18 are exemplary only. It should be clear that other dimensional configurations could be used to provide orthodontic arch wires of varying characteristics within the spirit of the present invention.

While FIGS. 13 and 14 illustrate the wound wire of FIGS. 1 and 2 in flattened form, the other wires of the invention could also be passed through rollers, or the like, so as to present a generally rectangular outer configuration. Such a generally rectangular configuration permits the orthodontic arch wires of the present invention to be useful for applying torquing forces to a tooth. Passing any of the spirally wound wires of FIGS. 1-12 through the orthogonally arranged pairs of rollers, for example as illustrated in FIG. 15, modifies the outer configuration thereof, for example by deforming the flanges so as to present a generally rectangular outer configuration. The generally rectangular wire can be used for torquing since it will non-rotatably fit within the opening 11 of the bracket 10, for example shown in FIG. 16.

The wires of FIGS. 17 and 18 could also be formed, for example by passing same through rollers, to present a generally rectangular outer configuration so as to be useful for providing torquing forces.

Figure 19:
FIG. 19 illustrates still another embodiment of of the present invention.

FIG. 19 illustrates a further embodiment of the present invention wherein a single rectangular strand is tightly wound into a spiral such that adjacent turns of the spiral abut each other. The arrangement of FIG. 19 clearly presents no lumen along the length of the wire. The wire of FIG. 19 is stiffer than, for example, the wire of FIG. 1, as should be apparent. Multiple strand arrangements could be tightly wound into a spiral as shown in FIG. 19. In particular, the arrangement of FIGS. 5 and 6 is particularly suitable for winding into a tightly wound spiral with adjacent turns contacting each other as shown in FIG. 19. The resulting structure would be similar in appearance to that of FIG. 19. It has been found that multi-strand composite wires are generally preferably to single strand arrangements.

As should be apparent from the above, the present invention provides orthodontic arch wires in a unique form which enables varying degrees of orthodontic forces to be obtained while still providing a composite wire with a substantially constant outer dimension so that it snugly fits within an opening of a bracket without excessive wobbling. This is an advantage as compared to solid and stranded wires since in the prior art wires the cross-sectional size is varied in order to provide different resiliencies so as to provide different orthodontic forces. As discussed above, this prior art technique is undesirable. The present invention enables providing variable amounts of wire material within a given outer dimensional size so as to provide varying forces with wires of substantially constant outer dimension.

The bracket shown in FIG. 16 is merely exemplary. Other orthodontic brackets can be used, for example such as the Begg-type bracket or any other orthodontic bracket with a wire receiving opening.

The maximum outer dimension of the formed wires in accordance with the present invention is generally limited to 0.045 inches. However, for most applications, it is sufficient to have a maximum outer dimension of 0.025 inches. This latter dimension is suitable for most orthodontic applications.

The generally rectangular strands shown in the drawings may take other shapes, for example oval or any other cross-sectional shape which presents a different bending force in two different directions. The round strands could also take different forms, as desired. The larger and smaller strands can be wound together, or one after another.

It should be clear that the various different strands of the composite orthodontic wires can be different types of metals having different bending characteristics. For example, it may be convenient to use a less resilient, but more formable strand wound together with a highly resilient strand, the resiliency of the total combination being more dependent upon the resilient strand and the formability of the overall combination being dependent upon the characteristics of the less resilient strand. Such composite structures permit tailoring the orthodontic arch wire to specific applications.

While the invention has been described above with respect to specific embodiments, it should be clear that various modifications and alterations may be made within the scope of the invention as defined in the appended claims.

I claim:

1. An orthodontic arch wire having a longitudinal axis, comprising:

at least one strand having first and second cross-sectional dimensions, one cross-sectional dimension being greater than the other, said at least one strand being spirally wound along said longitudinal axis so that adjacent turns of said spiral are separated from each other and such that said greater cross-sectional dimension of said at least one strand spirally winds longitudinally along said arch wire, said separation between adjacent turns of said at least one strand defining a substantially helically winding void space along said longitudinal axis, at least a portion of each helically winding void space being empty and devoid of wire material throughout the length of the wound arch wire, and said wound arch wire having a maximum common outer dimension no greater than approximately 0.045 inches and said at least one strand being made from a material sufficiently elastic to permit bending of the wound arch wire along the length thereof and to provide predetermined stiffness over a long length thereof so as to serve as an orthodontic arch wire.

2. An orthodontic arch wire according to claim 1, wherein said at least one strand is wound without a lumen.

3. An orthodontic arch wire according to claim 1, wherein said at least one strand is generally rectangular in cross-section.

4. An orthodontic arch wire according to claim 1, comprising a plurality of said strands, each of said strands having first and second cross-sectional dimensions, one cross-sectional dimension of each strand being greater than the other, said strands being adjacent to each other and spirally wound along said longitudinal axis with adjacent turns separated from each other.

5. An orthodontic arch wire according to claim 1, further comprising at least one further strand adjacent said at least one strand and spirally wound adjacent said at least one strand along said longitudinal axis.

6. An orthodontic arch wire according to claim 5, wherein said further strand has a generally round cross-section, and nests in the interstices formed by said at least one spirally wound strand.

7. An orthodontic arch wire according to claim 5, wherein said further strand has a smaller cross-section than said at least one strand, and it nests in the interstices formed by said at least one spirally wound strand.

8. An orthodontic arch wire according to claim 5, further comprising at least a second further strand adjacent said at least one strand and spirally wound adjacent said at least one strand along said longitudinal axis, said further strands having a smaller cross-section than said at least one spirally wound strand and said further strands being adjacent opposite larger cross-sectional dimension portions of said at least one spirally wound strand.

9. An orthodontic arch wire according to claim 8, wherein said further strands nest in the interstices formed by said at least one spirally wound strand.

10. An orthodontic arch wire according to claim 8, wherein said further strands have generally round cross-sections.

11. An orthodontic arch wire according to claim 8, further comprising at least a second strand of similar cross-sectional dimensions to said at least one spirally wound strand and located adjacent said at least one spirally wound strand.

12. An orthodontic arch wire according to claim 11, wherein said further strands are adjacent larger cross-sectional dimension portions of respective spirally wound strands.

13. An orthodontic arch wire having a longitudinal axis, comprising:

at least one strand having first and second cross-sectional dimensions, one cross-sectional dimension being greater than the other, said at least one strand having a substantially uniform cross-section along the length thereof and throughout the length of the arch wire, said at least one strand being spirally wound along said longitudinal axis so that adjacent turns of said spiral are separated from each other and such that said greater cross-sectional dimension of said at least one strand spirally winds longitudinally along said arch wire, said separation between said adjacent turns of said at least one strand defining a substantially helically winding void space along said longitudinal axis, at least a portion of each helically winding void space being empty and devoid of wire material throughout the length of the wound arch wire, and said wound arch wire having a maximum common outer dimension no greater than approximately 0.045 inches and said at least one strand being made from a material sufficiently elastic to permit bending of the wound arch wire along the length thereof and to provide predetermined stiffness over a long length thereof so as to serve as an orthodontic arch wire.

14. An orthodontic arch wire according to claim 13, wherein said at least one strand is wound without a lumen.

15. An orthodontic arch wire according to claim 13, wherein said at least one strand is generally rectangular in cross-section.

16. A orthodontic arch wire according to claim 13, comprising a plurality of said strands, each of said strands having first and second cross-sectional dimensions, one cross-sectional dimension of each strand being greater than the other, said strands each having a substantially uniform cross-section along the length thereof and throughout the length of the arch wire, said strands being adjacent to each other and spirally wound along said longitudinal axis with adjacent turns separated from each other to form said substantially helically winding void space between said adjacent turns.

17. An orthodontic arch wire according to claim 13, further comprising at least one further strand adjacent said at least one strand and spirally wound adjacent said at least one strand in said substantially helically winding space along said longitudnal axis.

18. An orthodontic arch wire according to claim 17, wherein said further strand has a generally round cross-section which is substantially uniform along the length of said further strand, said further strand nesting in the interstices formed by said at least one spirally wound strand.

19. An orthodontic arch wire according to claim 17, wherein said further strand has a smaller cross-section than said at least one strand, said smaller cross-section being substantially uniform along the length of said further strand, said further strand nesting in the interstices formed by said at least one spirally wound strand.

20. An orthodontic arch wire according to claim 17, further comprising at least a second further strand adjacent said at least one strand and spirally wound adjacent said at least one strand in said substantially helically winding space along said longitudinal axis, said further strands having a smaller cross-section than said at least one spirally wound strand and having a substantially uniform cross-section along the lengths thereof, said further strnds being adjacent opposite larger cross-sectional dimension portions of said at least one spirally wound strand.

21. An orthodontic arch wire according to claim 20, wherein said further strands nest in the interstices formed by said at least one spirally wound strand.

22. An orthodontic arch wire according to claim 20, wherein said further strands have generally round cross-sections.

23. An orthodontic arch wire according to claim 20, further comprising at least a second strand of similar cross-sectional dimensions to said at least one spirally wound strand and located adjacent said at least one spirally wound strand.

24. An orthodontic arch wire according to claim 23, wherein said further strands are adjacent larger cross-sectional dimension portions of respective spirally wound strands.

25. An orthodontic arch wire according to claim 1, wherein at least a portion of the strands are flattened so as to present a generally rectangular outer configuration.

26. An orthodontic arch wire according to claim 13, wherein said substantially helically winding space along said longitudinal axis is completely empty and devoid of wire material.

27. An orthondontic arch wire according to claim 13, wherein a substantial portion of each helically winding space is empty and devoid of wire.

28. An orthodontic arch wire according to claim 13, wherein said at least one strand, when spirally wound along said longitudinal axis, presents a generally round periphery.

29. An orthodontic arch wire according to claim 13, wherein said at least one strand, when spirally wound along said longitudinal axis, presents a generally rectangular outer configuration.

30. An orthodontic arch wire according to claim 3, wherein said helically wound arch wire has a generally round outer configuration.

31. An orthodontic arch wire having a longitudinal axis, comprising:

a single strand having first and second cross-sectional dimensions, one cross-sectional dimension being greater than the other, said single strand being spirally wound along said longitudinal axis such that said greater cross-sectional dimension of said single strand spirally winds longitudinally along said arch wire and that adjacent turns of said single strand abut each other, said single strand being wound substantially without a lumen, said wound wire having a maximum common outer dimension no greater than approximately 0.045 inches and said single strand being made from a material sufficiently elastic to permit bending of the wound arch wire along the length thereof and to provide predetermined stiffness over a long length thereof so as to serve as an orthodontic arch wire.

32. An orthodontic arch wire according to claim 31, wherein said single strand is generally rectangular in cross-section.

33. An orthodontic arch wire according to claim 31, wherein said single strand has a substantially constant cross-section throughout the length of said arch wire.

34. An orthodontic arch wire according to claim 31, wherein at least a portion of said strand is flattened so as to present a generally rectangular outer configuration.

35. An orthodontic arch wire according to claim 31, wherein said arch wire has a generally rectangular outer configuration.

36. An orthodontic arch wire according to claim 31, wherein said arch wire has a generally round outer configuration.

37. An orthodontic arch wire having a longitudinal axis, comprising:

a single strand having first and second cross-sectional dimensions, one cross-sectional dimension being greater than the other, said single strand being helically wound so as to form an array of successively overlapping turns, said wound strand having a maximum common outer dimension no greater than approximately 0.045 inches and said strand being made from a material sufficiently elastic to permit bending of the wound arch wire along the length thereof and to provide predetermined stiffness over a long length thereof so as to serve as an orthodontic arch wire.

38. An orthodontic arch wire according to claim 37, wherein said strand has a generally rectangular cross-section.

39. An orthodontic arch wire according to claim 37, wherein said strand is wound to form a lumen therethrough.

40. An orthodontic arch wire according to claim 37, wherein said helically wound arch wire has a generally rectangular outer configuration.

41. An orthodontic arch wire according to claim 37, wherein said helically wound arch wire has a generally round outer configuration.

* * * * *